US008663215B2

(12) United States Patent
Kabaya et al.

(10) Patent No.: US 8,663,215 B2
(45) Date of Patent: Mar. 4, 2014

(54) ELECTROSURGICAL APPARATUS AND METHOD FOR CONTROLLING ELECTROSURGICAL APPARATUS

(75) Inventors: Akinori Kabaya, Hachioji (JP); Takashi Mihori, Akiruno (JP)

(73) Assignee: Olympus Medical Systems Corp., Tokyo (JP)

( * ) Notice: Subject to any disclaimer, the term of this patent is extended or adjusted under 35 U.S.C. 154(b) by 1116 days.

(21) Appl. No.: 12/252,034

(22) Filed: Oct. 15, 2008

(65) Prior Publication Data

US 2010/0094276 A1    Apr. 15, 2010

(51) Int. Cl.
*A61B 18/12*    (2006.01)
(52) U.S. Cl.
USPC .......................................................... 606/40
(58) Field of Classification Search
USPC ............................. 606/21, 29, 33, 34, 41, 45
See application file for complete search history.

(56) References Cited

U.S. PATENT DOCUMENTS

| 6,464,696 | B1 | 10/2002 | Oyama et al. | |
| 2007/0276363 | A1* | 11/2007 | Patton et al. | 606/51 |
| 2008/0114351 | A1 | 5/2008 | Irisawa et al. | |
| 2008/0172052 | A1* | 7/2008 | Eder et al. | 606/50 |
| 2011/0077630 | A1* | 3/2011 | Tanaka et al. | 606/29 |

FOREIGN PATENT DOCUMENTS

| EP | 0 694 291 A1 | 1/1996 |
| EP | 1 917 927 A1 | 5/2008 |
| JP | 08-098845 | 4/1996 |
| JP | 08-317935 | 12/1996 |
| JP | 2000-254144 | 9/2000 |
| JP | 2002-065691 | 3/2002 |
| JP | 2002-325772 | 11/2002 |
| JP | 2004-008583 | 1/2004 |
| JP | 2004-229832 | 8/2004 |
| JP | 2007-143878 | 6/2007 |
| JP | 2008-114042 | 5/2008 |

OTHER PUBLICATIONS

International Search Report dated Nov. 17, 2009.
Extended Supplementary European Search Report dated Nov. 28, 2012 from related application EP 09820532.1-2305.

* cited by examiner

*Primary Examiner* — Nicholas Lucchesi
*Assistant Examiner* — Ian K. Holloway
(74) *Attorney, Agent, or Firm* — Scully, Scott, Murphy & Presser, P.C.

(57) ABSTRACT

A high-frequency cauterization power source is an electrosurgical apparatus for joining biological tissues. The electrosurgical apparatus includes a high frequency power supply portion for supplying a high frequency power that is applied to biological tissues; a detection portion for detecting a voltage and a current of a high frequency power that is output from the high frequency power supply portion; a tissue impedance calculating portion that calculates an impedance of biological tissue based on respective values for voltage and current detected at the detection portion; and a control portion that controls so as to substantially stop supply of the high frequency power from the high frequency power supply portion based on whether or not an increase greater than or equal to a predetermined value in the impedance that is calculated at the tissue impedance calculating portion occurs two times.

5 Claims, 12 Drawing Sheets

| LOW Z CONTINUATION TIME LZT | OUTPUT CONTINUATION TIME td AFTER Z RISE OF NEXT OUTPUT |
|---|---|
| ~ Tth2 | (OUTPUT TERMINATION) |
| Tth2 ~ Ta | 0 SECOND |
| Ta ~ Tb | 5 SECONDS |
| Tb ~ | 10 SECONDS |

ELECTROSURGICAL APPARATUS AND METHOD FOR CONTROLLING ELECTROSURGICAL APPARATUS

BACKGROUND OF THE INVENTION

1. Field of the Invention

The present invention relates to an electrosurgical apparatus for treating biological tissue and a method for controlling the electrosurgical apparatus, and more particularly to an electrosurgical apparatus for joining biological tissues and a method for controlling the electrosurgical apparatus.

2. Description of Related Art

Electrosurgical apparatuses are already widely used for surgical operations and the like. For example, electrosurgical apparatus are utilized in surgical operations to perform treatment such as dissecting biological tissue or joining tissues that have been dissected.

More specifically, a treatment instrument connected to a high frequency power source is brought in contact with the biological tissue that is the treatment target so that a high frequency power from the high frequency power source is supplied to the treatment instrument to thereby dissect or join the tissue that is the treatment target.

This kind of electrosurgical apparatus has already been proposed in various publications. For example, Japanese Patent Application Laid-Open Publication No. 8-98845 or Japanese Patent Application Laid-Open Publication No. 2002-325772 proposes an electrosurgical apparatus that is designed to prevent carbonization of coagulating biological tissue, determine the end of coagulation based on the impedance of the biological tissue, and then stop the high-frequency output.

SUMMARY OF THE INVENTION

An electrosurgical apparatus according to one aspect of the present invention is an electrosurgical apparatus for joining biological tissues that includes: a high frequency power supply portion for supplying a high frequency power that is applied to the biological tissues; a detection portion for detecting a voltage and a current of the high frequency power that is output from the high frequency power supply portion; a tissue impedance calculating portion that calculates an impedance of the biological tissues based on respective values of the voltage and the current that are detected by the detection portion; and a control portion that, based on whether or not an increase that is equal to or greater than a predetermined value in the impedance that is calculated by the tissue impedance calculating portion occurs two times, controls to supply, stop supply of, or substantially stop supply of the high frequency power from the high frequency power supply portion.

A method for controlling an electrosurgical apparatus according to another aspect of the present invention is a method for controlling an electrosurgical apparatus to join biological tissues, wherein control is performed to detect a voltage and a current of a high frequency power output from a high frequency power supply portion for supplying the high frequency power to be applied to the biological tissues, calculate an impedance of the biological tissues based on respective values of the voltage and the current that are detected, and supply, stop supply of, or substantially stop supply of the high frequency power from the high frequency power supply portion based on whether or not an increase that is equal to or greater than a predetermined value in the calculated impedance occurs two times.

DETAILED DESCRIPTION OF THE PREFERRED EMBODIMENTS

Embodiments of the present invention are described hereunder referring to the attached drawings.

First Embodiment

Figure 1:
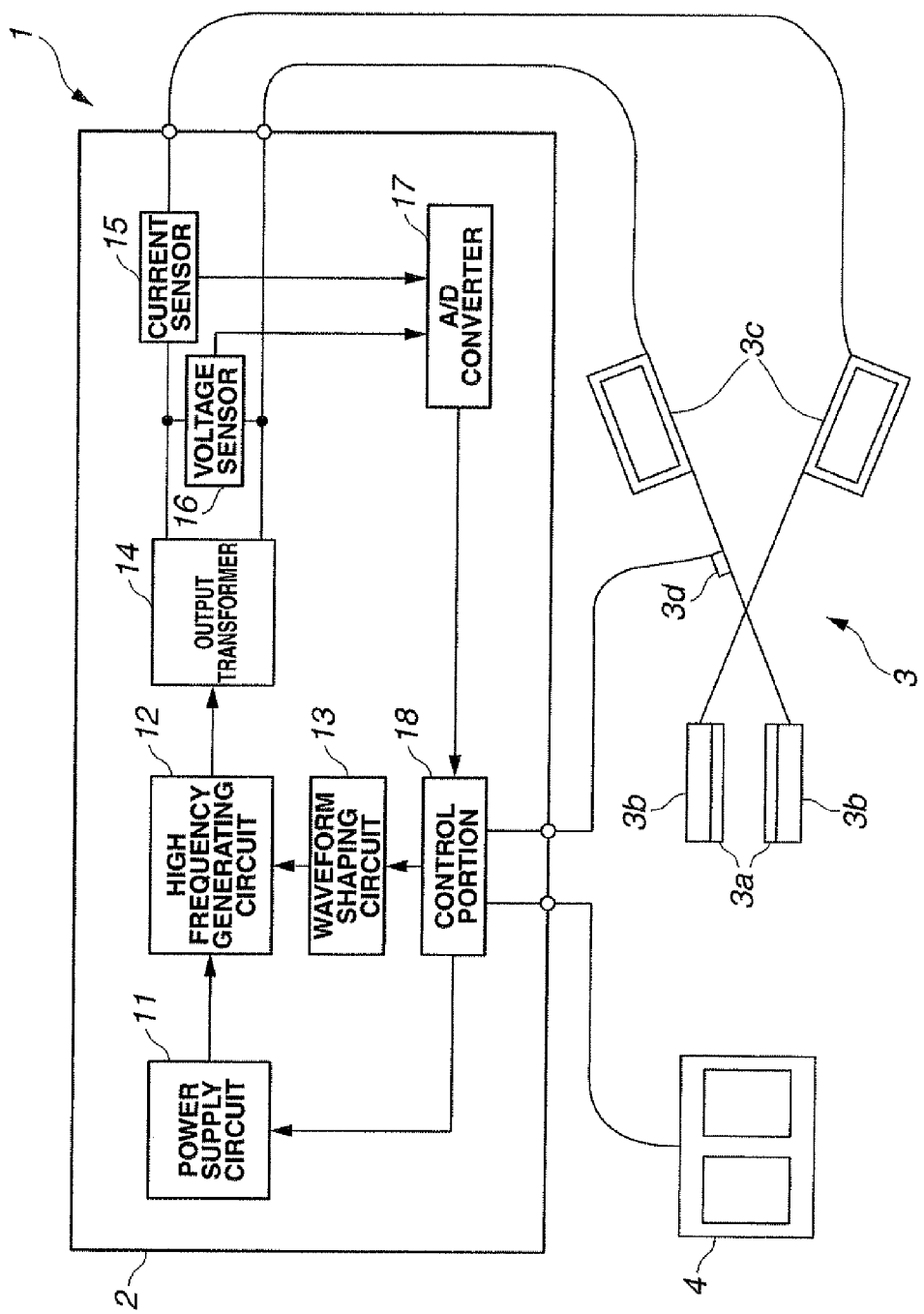
FIG. 1 is a view for describing the configuration of an electrosurgical system according to a first embodiment of the present invention.

FIG. 1 is a view for describing the configuration of an electrosurgical system according to a first embodiment of the present invention.

An electrosurgical system 1 according to the present embodiment includes a high-frequency cauterization power source 2 as an electrosurgical apparatus for joining biological tissues, a treatment instrument 3 that supplies a high frequency power from the high-frequency cauterization power source 2 to biological tissue of a patient, and a foot switch 4 with which a physician performs control to switch the high frequency power on and off. The treatment instrument 3 is a bipolar forceps that has a pair of sandwiching portions 3b that are provided with a pair of electrodes 3a, and grasping portions 3c. A hand switch 3d is provided in the treatment instrument 3. The hand switch 3d and the foot switch 4 are connected to the high-frequency cauterization power source 2.

The physician sandwiches biological tissues to be joined between the pair of electrodes 3a of the pair of sandwiching portions 3b provided at the distal end portion of the treatment instrument 3 by performing an operation to close the treatment instrument 3 while grasping the grasping portions 3c, and then switches on the hand switch 3d or the foot switch 4 with the biological tissues still in that sandwiched state. When the foot switch 4 or the like is turned on, a high frequency power is supplied to the biological tissues that are grasped by the pair of electrodes 3a, to thereby join the biological tissues.

The high-frequency cauterization power source 2 includes a power supply circuit 11 that supplies direct-current electricity, a high frequency generating circuit 12 that converts the direct-current electricity from the power supply circuit 11 into a high-frequency current, a waveform shaping circuit 13 for controlling waveforms of the high-frequency current that is output from the high frequency generating circuit 12, an output transformer 14 that outputs the high-frequency current from the high frequency generating circuit 12 to the pair of electrodes 3a, a current sensor 15 that detects an output electrical current that is output by the output transformer 14, a voltage sensor 16 that detects an output voltage that is output by the output transformer 14, an A/D converter 17 that performs A/D conversion of an electrical current value and a voltage value that are detected by the current sensor 15 and the voltage sensor 16, and a control portion 18 that controls the power supply circuit 11 and the waveform shaping circuit 13 using electrical current and voltage data that has been digitized by the A/D converter 17.

The power supply circuit 11, the high frequency generating circuit 12, the waveform shaping circuit 13, and the output transformer 14 constitute a high frequency power supply portion for supplying high frequency power. The current sensor 15, the voltage sensor 16, and the A/D converter 17 constitute a detection portion that detects the voltage and the current of high frequency power that is output from the high frequency power supply portion. The control portion 18 comprises a tissue impedance calculating portion that calculates an impedance in biological tissue based on respective values for voltage and current that are detected at the detection portion, and as described later, performs various control based on the calculated impedance value.

The control portion 18 includes a CPU and a memory and the like. Based on input commands and data, the control portion 18 performs predetermined processing by executing a program that is previously stored in the memory. Furthermore, during an operation, various kinds of data are displayed and sounds and warning sounds are output using a monitor and a speaker and the like (not shown) that are connected to the control portion 18.

The high-frequency cauterization power source 2 supplies high frequency power to the pair of electrodes 3a. The temperature of tissue that receives the high frequency power rises and the impedance of the tissue changes. In order to appropriately join the tissues in accordance with a change in the impedance, the high-frequency cauterization power source 2 combines the use of constant power control and constant voltage control when controlling output of the high frequency power.

Figure 2:
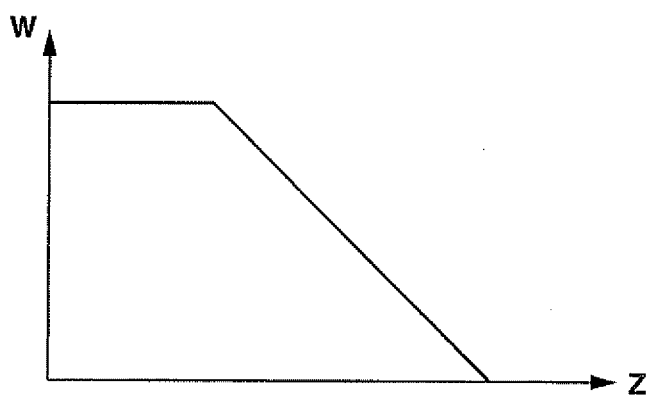
FIG. 2 is a graph for describing output control of high-frequency output that is output from a high-frequency cauterization power source according to the first embodiment of the present invention.

FIG. 2 is a graph for describing output control of a high-frequency output that is output from the high-frequency cauterization power source 2. In FIG. 2, the axis of ordinates represents power and the axis of abscissas represents an impedance z. As shown in FIG. 2, after starting output of a high frequency power, constant power control is used to control the power of the high frequency power since the impedance of the tissue is low. Subsequently, after the impedance of the tissue rises, i.e. increases, to reach a predetermined state as described later, the power of the high frequency power is controlled using constant voltage control. This is done to prevent transformation of the tissue due to the occurrence of electric discharge when the impedance rises.

The electrosurgical system 1 is configured so that joining of tissues can be appropriately carried out in a short time by controlling the output of high frequency power in this manner, when there is a change in the impedance of the tissue.

Next, a treatment method according to the present embodiment is described.

Figure 3:
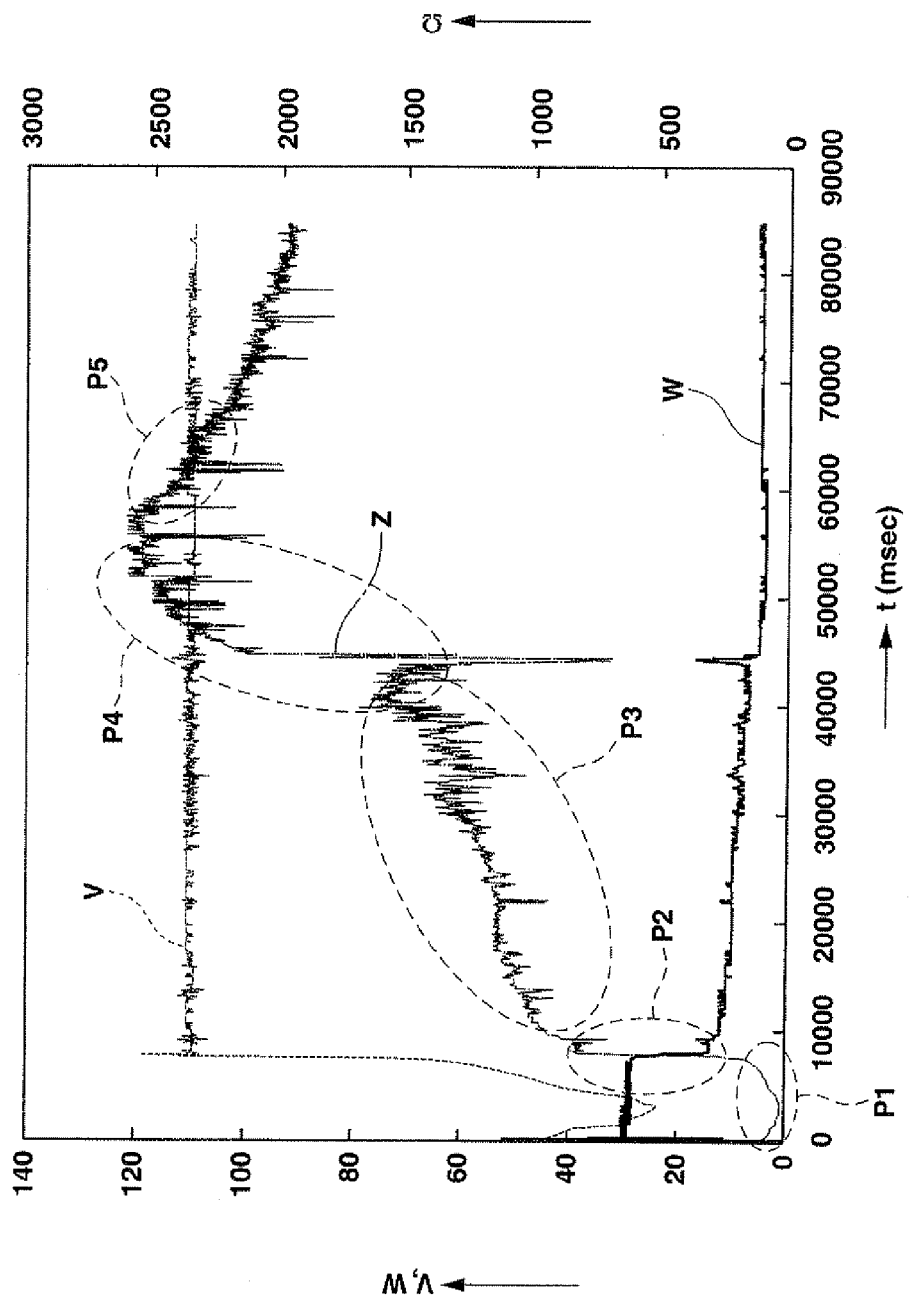
FIG. 3 is a graph that illustrates an example of changes in the output power and output voltage of a high frequency power and in the impedance of tissue in a case in which joining of tissue in the digestive tract is performed according to the first embodiment of the present invention.

FIG. 3 is a graph that illustrates an example of changes in the output power and output voltage of high frequency power and in the impedance of tissue in a case of joining tissues in the digestive tract.

Under constant power control, when output of a high frequency power is started, Joule heat occurs in the tissue that receives the high frequency power and the temperature of the tissue rises. When the tissue temperature rises, the movement of ions inside the tissue becomes active, and thus the impedance Z of the tissue decreases.

However, at a point where the impedance Z reaches the minimum level, the tissue temperature is highest and evaporation of moisture within the tissue begins, and thus the tissue impedance Z starts to rise. Since vapor is an insulator electrically, the impedance Z rises when generation of vapor begins within the tissue.

The section described above is the section denoted by reference numeral P1 in FIG. 3.

Thereafter, when a vapor layer is formed across the entire inside of the tissues that are grasped by the pair of electrodes 3a of the treatment instrument 3, the impedance Z of the tissues rises sharply. It is considered that the rise in the impedance Z at this time is not a phenomenon that indicates the state of the tissues, but is a phenomenon that indicates that a vapor layer has been generated in the tissues. When the sharp rise in the impedance Z occurs, the generation of vapor within the tissue is at the most intense level. Therefore, when this first sharp rise in the impedance Z is detected, control of output of the high frequency power is changed to constant voltage control.

The section described above is the section denoted by reference numeral P2 in FIG. 3.

Although the impedance of the tissue rises thereafter also, it is considered that the rising impedance does not indicate the state of the tissue, but rather indicates the presence of vapor in the tissue. Although the power supplied to the tissue decreases accompanying a rise in impedance under the constant voltage control, a high frequency power is supplied little by little to a section with residual moisture inside the tissues that are grasped by the pair of electrodes 3a and a non-cauterized section at the periphery of the pair of electrodes 3a. As the moisture of these sections evaporates little by little, the impedance gradually rises. At this time, vapor-generating sound is, although small, continuously generated.

The section described above is the section denoted by reference numeral P3 in FIG. 3.

Thereafter, when moisture is completely removed from the tissue, including the section at the periphery of the pair of electrodes 3a, the tissue enters a dehydrated state and the impedance Z of the tissue sharply rises again. As a result, the high frequency power that is supplied to the tissue decreases further, and hence the temperature of the tissue begins to drop and the vaporization sound is no longer generated. This section is denoted by reference numeral P4 in FIG. 3.

Thereafter, since vapor is not generated and the vapor that was formed until that time disappears, the impedance Z of the tissue decreases. This section is denoted by reference numeral P5 in FIG. 3.

Thus, the electrosurgical system 1 according to the present embodiment performs control so as to stop output of a high frequency power when there is a second sharp rise in the impedance Z or when the impedance Z falls after that rise (section denoted by reference numeral P4 or section denoted by reference numeral P5), on the assumption that the tissue has entered a dehydrated state.

Conventionally, with respect to the section denoted by reference numeral P2, there have been cases in which although detection is performed to determine whether or not the impedance Z has reached a predetermined threshold value or more and the output of a high frequency power has been stopped, the joining force of the tissues has been weak because the tissues at the joining portion are not in a dehydrated state. Further, although supply of a high frequency power to the tissues may be continued after the impedance Z has reached a predetermined threshold value or more, a problem arises that if the supply is continued for an excessively long time there is a possibility of exceeding a dehydrated state so that the tissues are burnt, for example, and moreover the operation time becomes unnecessarily long.

Therefore, according to the present embodiment it is possible to detect that a tissue has entered a dehydrated state according to the above described conditions, and also to prevent problems of such tissue being burnt due to a high frequency power supplied over a long time, without any weakening of the joining force when joining tissues.

Next, the aforementioned processing is described. In the processing described below, the control portion 18 is implemented using software. As described hereunder, the control portion 18 is configured to control supply and stoppage of a high frequency power based on whether or not there is an increase two times, which is equal to or greater than a predetermined value in the impedance Z.

Figure 4:
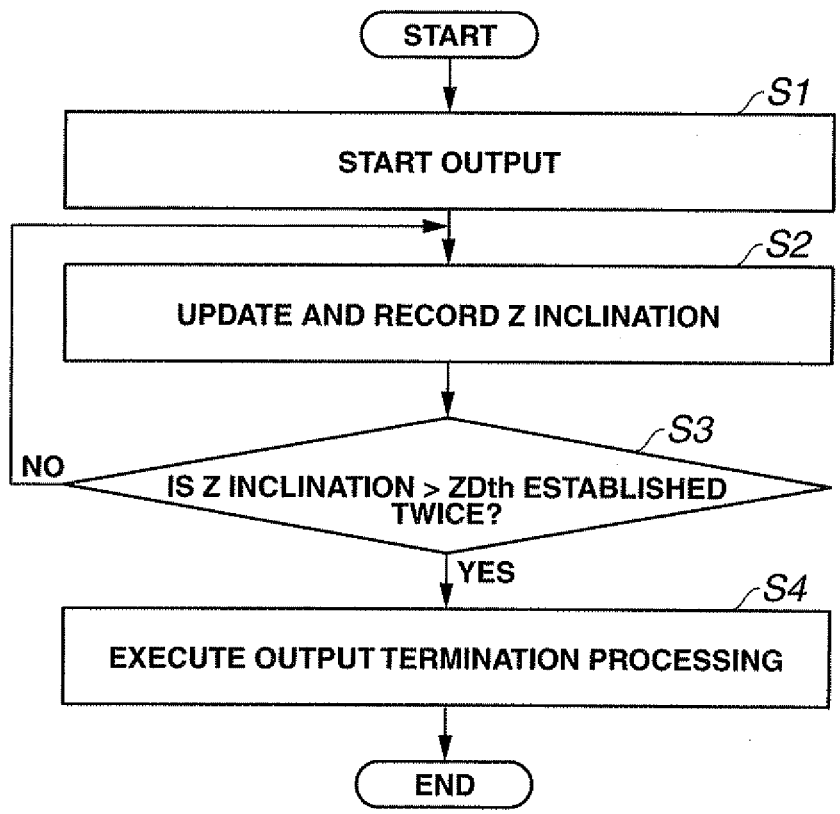
FIG. 4 is a flowchart that illustrates an example of a processing flow for determining a dehydration state of tissue at a section denoted by reference numeral P4 in FIG. 3.

FIG. 4 is a flowchart that illustrates an example of a processing flow for determining a dehydration state of tissue at a section denoted by reference numeral P4 in FIG. 3.

The processing of the flowchart shown in FIG. 4 is started when the foot switch 4 or the like is pressed.

First, the control portion 18 turns on the power supply circuit 11 to output a predetermined signal to the waveform shaping circuit 13, to thereby start output of high frequency power from the output transformer 14 (step S1).

Thereafter, the control portion 18 calculates and monitors the impedance Z of tissue based on electrical current value data and voltage value data input from the A/D converter 17.

The control portion 18 calculates the rate of change, i.e. inclination (hereafter referred to as "Z inclination"), of the impedance Z as an impedance value obtained by the calculation at step S1, and records the calculated Z inclination in the memory (step S2).

Data for a threshold value ZDth of the impedance Z is stored in the memory, and the control portion 18 determines whether the Z inclination has exceeded the threshold value ZDth two times (step S3).

In this connection, the threshold value ZDth is set to a value that enables detection of the time of a first and a second sharp impedance rise as shown in FIG. 3.

When the number of times that the Z inclination has exceeded the threshold value ZDth does not reach two times, i.e. when the relation Z inclination>ZDth is not established twice, the result at step S3 is "NO", and the processing returns to step S2.

More specifically, the control portion 18 decides whether or not there is an increase that is equal to or greater than a predetermined value in the impedance Z by determining the rate of change per unit time in the impedance Z and comparing that determined rate of change and the predetermined threshold value ZDth.

For example, the threshold value ZDth is set to a value with which, in the aforementioned graph in FIG. 3, a sharp rise in the impedance Z in section P2 can be determined and also with which a sharp rise in impedance Z in section P4 can be determined, and that value is previously stored in a memory (not shown) of the control portion 18.

As shown in FIG. 3, after starting output of a high frequency power, at section P2, even if there is a sharp rise in the impedance Z and the impedance Z exceeds the threshold value ZDth, since this is only the first time that the impedance Z exceeds the threshold value ZDth, the result at step S3 is not "YES". Thereafter, the control portion 18 continues to perform the processing of steps S2 and S3.

More specifically, the control portion 18 assumes that the first increase after a decrease in the impedance Z after starting the supply of high frequency power is an increase that is equal to or greater than a predetermined value in the impedance Z for the first of two times, and thus the result is not "YES" at step S3.

In this connection, separately to the above described processing, the control portion 18 detects the first sharp rise in the impedance Z and, by separate control processing, performs control to change the output control from constant power control to constant voltage control.

Subsequently, when there is a sharp rise in the impedance Z at the section P4 in FIG. 3 and the impedance Z exceeds the threshold value ZDth, because this is the second time that the impedance Z exceeds the threshold value ZDth, the result at step S3 is "YES", and output termination processing is then executed (step S4).

For the output termination processing, a configuration may be adopted in which a buzzer sound or the like is output from a speaker to notify the physician that the tissue has entered a dehydrated state and the output of the high frequency power is also stopped, or the output of the high frequency power may be stopped without outputting a buzzer sound or the like from the speaker. As used herein, the term "stopping output" also includes a substantially stopped state such as a state in which a low level of a high frequency power that does not cauterize tissue is output.

Further, for the output termination processing, a configuration may also be adopted in which a buzzer sound or the like is output from a speaker to notify the physician that the tissue has entered a dehydrated state, and thereafter output of the high frequency power is stopped when the physician inputs an "off" command using the foot switch 4 or the like.

Thus, a dehydration state of tissue at the section denoted by reference numeral P4 can be determined by means of the above described operations.

Hence, the control portion 18 performs control so as to stop the supply of high frequency power when there is an increase equal to or greater than a predetermined value in the impedance Z for a second time among the two times.

Figure 5:
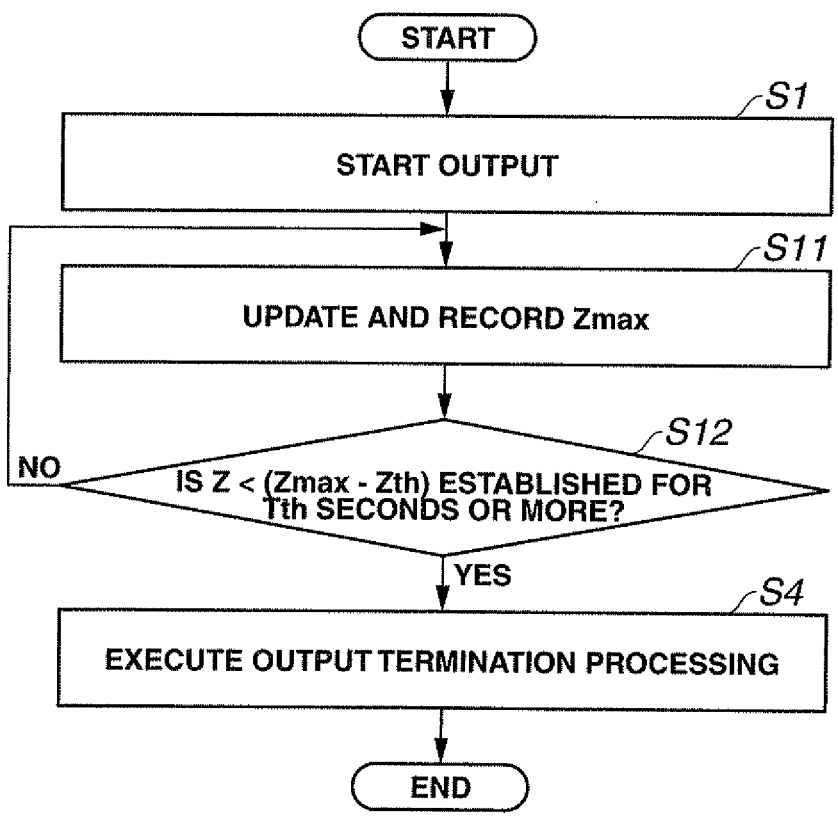
FIG. 5 is a flowchart that illustrates an example of a processing flow for determining a dehydration state of tissue at a section denoted by reference numeral P5 in FIG. 3.

FIG. 5 is a flowchart that illustrates an example of a processing flow for determining a dehydration state of tissue at the section denoted by reference numeral P5 in FIG. 3. In the flowchart in FIG. 5, processing that is the same as the processing in FIG. 4 is denoted by the same reference numeral, and a description of that processing is partly omitted.

The processing of the flowchart shown in FIG. 5 is also started when the foot switch 4 or the like is pressed.

First, the control portion 18 turns on the power supply circuit 11 to output a predetermined signal to the waveform shaping circuit 13, to thereby start output of high frequency power from the output transformer 14 (step S1).

Thereafter, the control portion 18 calculates and monitors the impedance Z of tissue based on electrical current value data and voltage value data input from the A/D converter 17.

The control portion 18 stores the thus-calculated impedance Z, updates a maximum value Zmax in the stored impedance Z, and records the updated value Zmax in the memory (step S11).

Data for a predetermined threshold value Zth relating to the impedance Zmax and a predetermined threshold value Tth relating to time are stored in the memory. The control portion 18 determines whether or not a state in which the impedance Z is less than (Zmax−Zth) has continued for a Tth time or more, for example, Tth seconds or more (step S12).

When a state in which the impedance Z is less than a value that is smaller than the impedance Zmax by the amount of the threshold value Zth does not continue for the predetermined time Tth or more, i.e. when the relation Z<(Zmax−Zth) is not established for the Tth time or more, the result at step S12 is "NO" and the processing returns to step S11.

For example, the threshold values Zth and Tth are set to values that make it possible to determine that, in section P5 in the graph of the aforementioned FIG. 3, the impedance Z is starting to gradually drop, and these values are previously stored in the memory (not shown) of the control portion 18.

As shown in FIG. 3, after starting output of a high frequency power, even if there is a momentary drop in the impedance Z at sections P3 and P4, unless the drop continues for the predetermined time Tth or more, the result is not "YES" at step S12. Thereafter, the control portion 18 continues to perform the processing of steps S11 and S12.

In this connection, when executing the processing described in FIG. 5 also, separately to the above described processing, the control portion 18 detects the first sharp rise in the impedance Z and, by separate control processing, performs control to change the output control from constant power control to constant voltage control.

When the impedance Z gradually declines in section P5 of FIG. 3, and a state in which the impedance Z is less than a value that is smaller than the impedance Zmax by the amount of the threshold value Zth continues for the predetermined time Tth or more, the result at step S12 is "YES" and output termination processing is then executed (step S4).

The foregoing processing makes it possible to determine dehydration of tissue at the section denoted by reference numeral P5.

Hence, the control portion 18 controls so as to stop the supply of the high frequency power when there is a decrease in the impedance Z after an increase that is equal to or greater than a predetermined value in the impedance Z for a second time of two times.

In this connection, in the aforementioned examples, in the cases shown in FIG. 4 and FIG. 5, respectively, a process to terminate output of the high frequency power is performed by outputting a buzzer sound or the like from a speaker to notify the physician that tissue is in a dehydrated state and also stopping output of the high frequency power, or by stopping output of the high frequency power without outputting a buzzer sound or the like from a speaker, or, furthermore, by outputting a buzzer sound or the like from a speaker to notify the physician that tissue is in a dehydrated state and thereafter stopping output of the high frequency power upon input of an "off" command using the foot switch 4 or the like by the physician.

The electrosurgical system 1 may also be configured to perform processing that combines the processing of FIG. 4 and FIG. 5 described above. In that case, the output termination processing can be performed in the following manner based on two dehydration states that are detected.

In this connection, a determination by detection of a sharp rise in impedance according to FIG. 4 is referred to as "determination A" and a determination by detecting that the impedance gradually drops in accordance with FIG. 5 is referred to as "determination B". More specifically, determination A is determination of a state in which the impedance Z increases by a predetermined value or more for a second time, and determination B is determination of a decreasing state in the impedance after the impedance Z increases by a predetermined value or more for a second time.

Any of the following kinds of processing is performed as output termination processing.

a) In response to occurrence of the determination type that is previously set by a physician or the like from determination A or determination B, the control portion 18 notifies the physician with a buzzer sound or the like and stops output of high frequency power.

b) The control portion 18 notifies the physician of the occurrence of determination A with a buzzer sound or the like, and thereafter, when the physician inputs an "off" command using the foot switch 4 or the like before occurrence of determination B, i.e. when a signal to stop output is received, the control portion 18 stops output of the high frequency power. In this connection, when an "off" command is not input before occurrence of determination B, in response to occurrence of determination B the control portion 18 notifies the physician thereof using a buzzer sound or the like, or stops output of the high frequency power without notifying the physician with a buzzer sound or the like.

c) The control portion 18 notifies the physician of the occurrence of determination A using a buzzer sound or the like, and thereafter, in response to occurrence of determination B, the control portion 18 notifies the physician thereof using a buzzer sound or the like and stops output of the high frequency power.

As described above, according to the electrosurgical apparatus of the present embodiment, when joining tissues, since it is possible to detect a dehydrated state of the tissues and stop output of the high frequency power, the joint between the tissues does not weaken.

Second Embodiment

Next, a second embodiment of the present invention is described.

According to the present embodiment, supply of a high frequency power and supply of a predetermined electrical voltage are alternately performed in response to changes in impedance during the supply of the high frequency power, the impedance of tissue in the predetermined electrical voltage supplying period is measured, and drying of tissue is determined by detecting that the measured impedance is equal to or greater than a predetermined threshold value.

The configuration of the apparatus of the present embodiment is the same as that of the electrosurgical system 1 of the first embodiment shown in FIG. 1. Hence, components that are the same as in the first embodiment are denoted by the same reference numerals and a description of those components is omitted.

Figure 6:
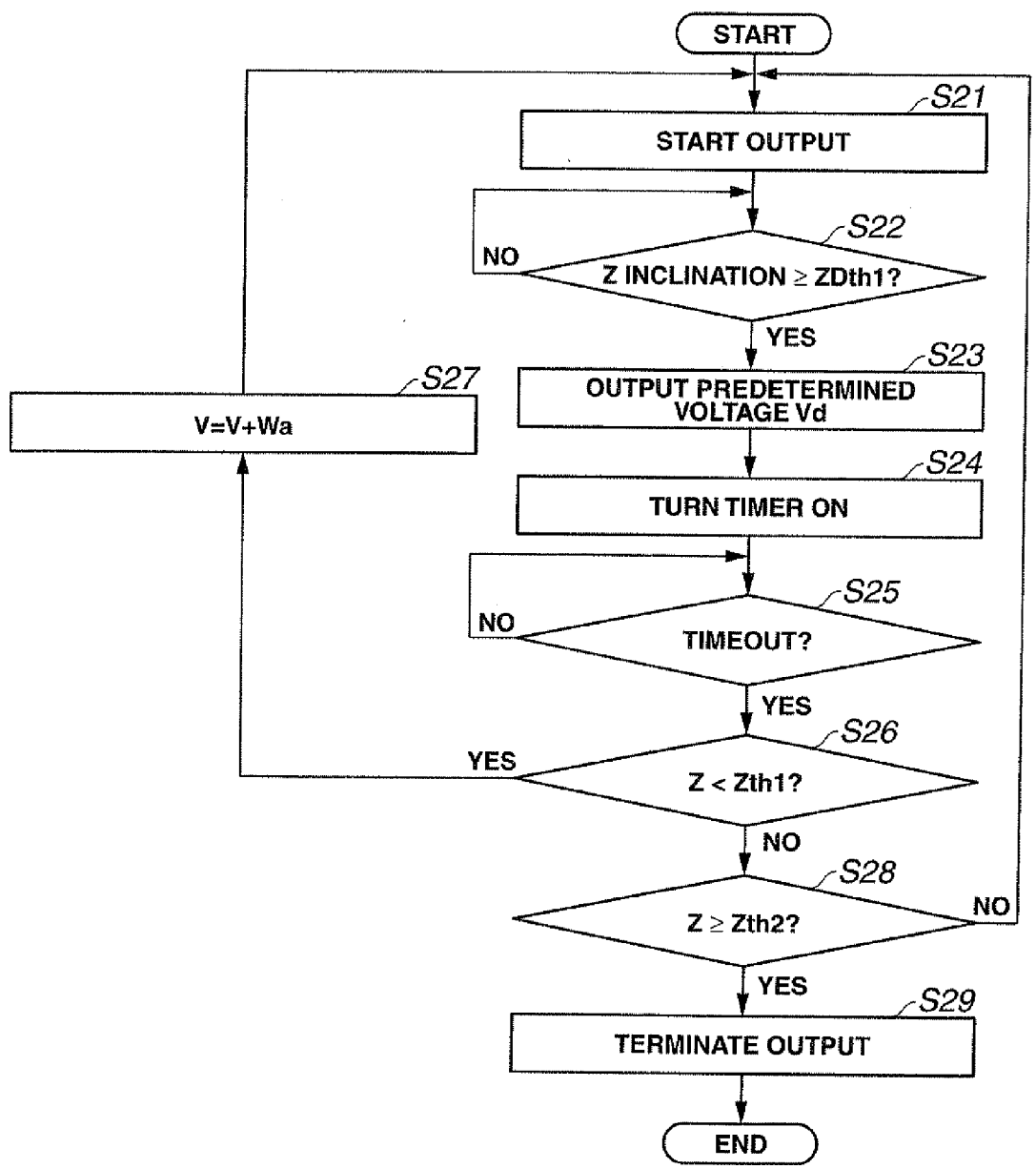
FIG. 6 is a flowchart that illustrates an example of a processing flow for determining a dehydration state of tissue according to a second embodiment of the present invention.
Figure 7:
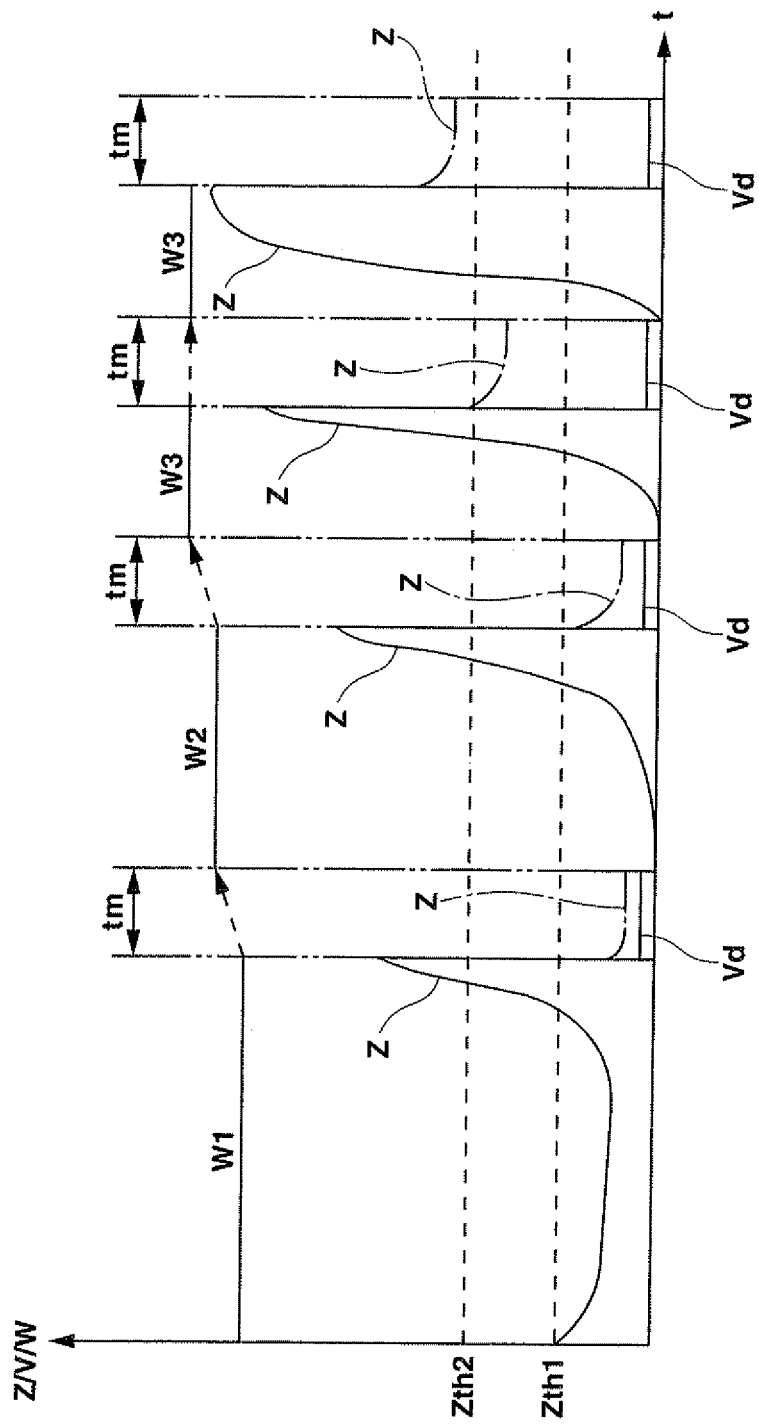
FIG. 7 is a graph that illustrates an example of changes accompanying the elapsed time in an impedance Z and an output power or a voltage according to the second embodiment of the present invention.

FIG. 6 is a flowchart that illustrates an example of a processing flow for determining a dehydration state of tissue according to the present embodiment. FIG. 7 is a graph that illustrates an example of changes accompanying the elapsed time in impedance Z and the output power or the voltage.

The processing of the flowchart shown in FIG. 6 starts when the foot switch 4 or the like is pressed.

First, the control portion 18 turns on the power supply circuit 11 to output a predetermined signal to the waveform shaping circuit 13, and thereby start output of high frequency power of a predetermined power value W1 from the output transformer 14 (step S21).

Thereafter, the control portion 18 calculates and monitors the impedance Z of tissue based on electrical current value data and voltage value data input from the A/D converter 17.

In this connection, similarly to the first embodiment, the output control is performed so as to start from constant power control, and then switch to constant voltage control when the impedance Z reaches a predetermined value or more.

The control portion 18 calculates the Z inclination as the rate of change in the impedance Z that is the impedance value that has been obtained by calculation, and determines whether or not the Z inclination is equal to or greater than a predetermined threshold value ZDth1 (step S22). In this connection, whether or not the Z inclination is equal to or greater than the predetermined threshold value ZDth1 is determined by performing processing such as eliminating a noise signal, similarly to the first embodiment.

A configuration may also be adopted in which, at step S22, the control portion 18 determines whether or not the calculated impedance value is equal to or greater than a predetermined threshold value TH. The predetermined threshold value TH and the above described threshold value ZDth1 are set to values that enable detection of the time of the first sharp rise in impedance shown in FIG. 3.

In FIG. 7, although the impedance Z temporarily drops immediately after the start of power output, thereafter the impedance Z rises accompanying evaporation of moisture in the tissue.

When the Z inclination is less than ZDth1, the result at step S22 is "NO", and no processing is performed.

When the Z inclination is greater than or equal to ZDth1, the result at step S22 is "YES", and instead of the power W1, a predetermined voltage Vd is output (step S23).

As shown in FIG. 7, when the Z inclination as the inclination in the impedance Z when there is a rise in impedance Z is greater than or equal to the predetermined threshold value ZDth1, output of high frequency power is changed from the predetermined power value W1 to the predetermined voltage Vd.

Next, the control portion 18 turns on a timer (step S24). The timer is a timer for a predetermined time tm, and is configured to time out when the predetermined time tm lapses. The timer may be constituted of hardware or software.

Subsequently, the control portion 18 determines whether or not the timer has timed out (step S25), and unless the timer has timed out, no processing is performed. Upon the timer timing out, the control portion 18 determines whether or not the measured impedance Z is less than the predetermined threshold value Zth1 (step S26).

When the impedance Z is less than the predetermined threshold value Zth1, the control portion 18 calculates the power to be supplied in the next high-frequency output period by adding a predetermined power value Wa to a supply power value W, for example, the mean power value, of the previous output period (step S27), and the processing then returns to step S21. As a result, output of a high frequency power of the addition value (W+Wa) is started (S21). If the supplied power value for the first high frequency power output period is W1, then in the second output period a voltage with a power value (W2=W1+Wa) is supplied.

More specifically, when the impedance Z in a period in which a high frequency power is not supplied is less than the predetermined threshold value Zth1 that is smaller than a predetermined threshold value Zth2 that is described later, the control portion 18 increases the power value of high frequency power to be supplied in the next high frequency power supply period by a predetermined amount Wa.

Accordingly, the fact that the impedance Z at the final time point of the output period of the predetermined voltage Vd is less than the threshold value Zth1 means that a lot of moisture remains inside the tissue. Hence, in order to dry the tissue in a short time the output power is increased, and the amount of that increase is Wa. In FIG. 7, the reason that the power in the second period of outputting a high frequency power increases from W1 to W2 is that, since the impedance Z indicated by the dashed line is less than the threshold value Zth1, drying of tissue is speeded up. Similarly, in the third output period also, the power rises from W2 to W3.

When the impedance Z is greater than or equal to the predetermined threshold value Zth1, the result at step S26 is "YES". Next, the control portion 18 determines whether or not the impedance Z is greater than or equal to the predetermined threshold value Zth2 (step S28).

When the impedance Z is not greater than or equal to the predetermined threshold value Zth2, the result at step S29 is "NO" and the processing returns to step S21.

More specifically, when the impedance Z in a period in which a high frequency power is not supplied is less than the predetermined threshold value Zth2 and is greater than or equal to the predetermined threshold value Zth1, the control portion 18 does not change the power value of high frequency power to be supplied in the next high frequency power supply period.

When the impedance Z in the output period of the predetermined voltage Vd is greater than or equal to the threshold value Zth1 and less than the threshold value Zth2, it means that most of a lot of moisture inside the tissue has been evaporated and that a drop in the impedance Z can no longer be observed, and that it is not of a degree that the voltage should be increased further to speed up the tissue drying time. Hence, in FIG. 7, the power in the fourth period of outputting a high frequency power remains at W3.

When the impedance Z is greater than or equal to the predetermined threshold value Zth2, the result at step S28 is "YES", and the control portion 18 stops output of the high frequency power (step S30).

The fact that the impedance Z in the output period of the predetermined voltage Vd is greater than or equal to the threshold value Zth2 indicates that the tissue is in a dry state, and hence the output of high frequency power is stopped.

As described above, the control portion 18 controls to intermittently supply a high frequency power after there is an increase by a predetermined value or more in the calculated impedance Z, and when the impedance Z during a high frequency power supply period in which a high frequency power is not being supplied reaches a value that is greater than or equal to the predetermined threshold value Zth2, the control portion 18 controls to stop the supply of the high frequency power.

Accordingly, with the electrosurgical system 1 of the present embodiment also, since output of high frequency power is stopped by detecting a dry state of tissue, joining of tissue with a strong joining force can be performed.

Third Embodiment

Next, a third embodiment of the present invention is described.

According to the present embodiment, control is performed to alternately supply and stop supply of a high frequency power, and drying of tissue is determined by detecting that a time until an impedance Z during supply of the high frequency power reaches a value greater than or equal to a predetermined threshold value, i.e. a low impedance continuation time LZT, is less than a predetermined time.

The configuration of the apparatus of the present embodiment is the same as the configuration of the electrosurgical system 1 of the first embodiment as shown in FIG. 1. Hence, components that are the same as in the first embodiment are denoted by the same reference numerals and a description of those components is omitted.

Figure 8:
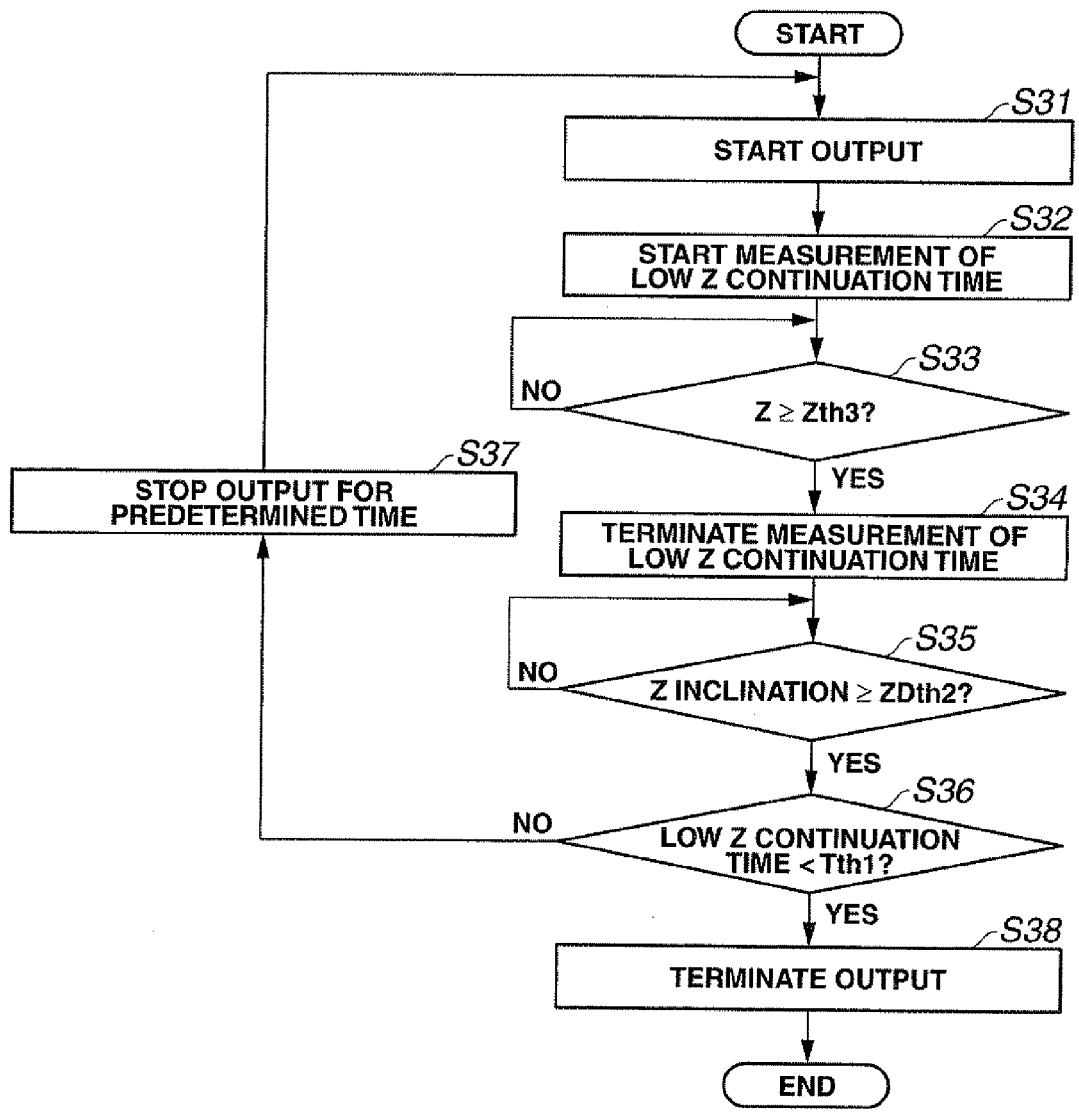
FIG. 8 is a flowchart that illustrates an example of a processing flow for determining a dehydration state of tissue according to a third embodiment of the present invention.
Figure 9:
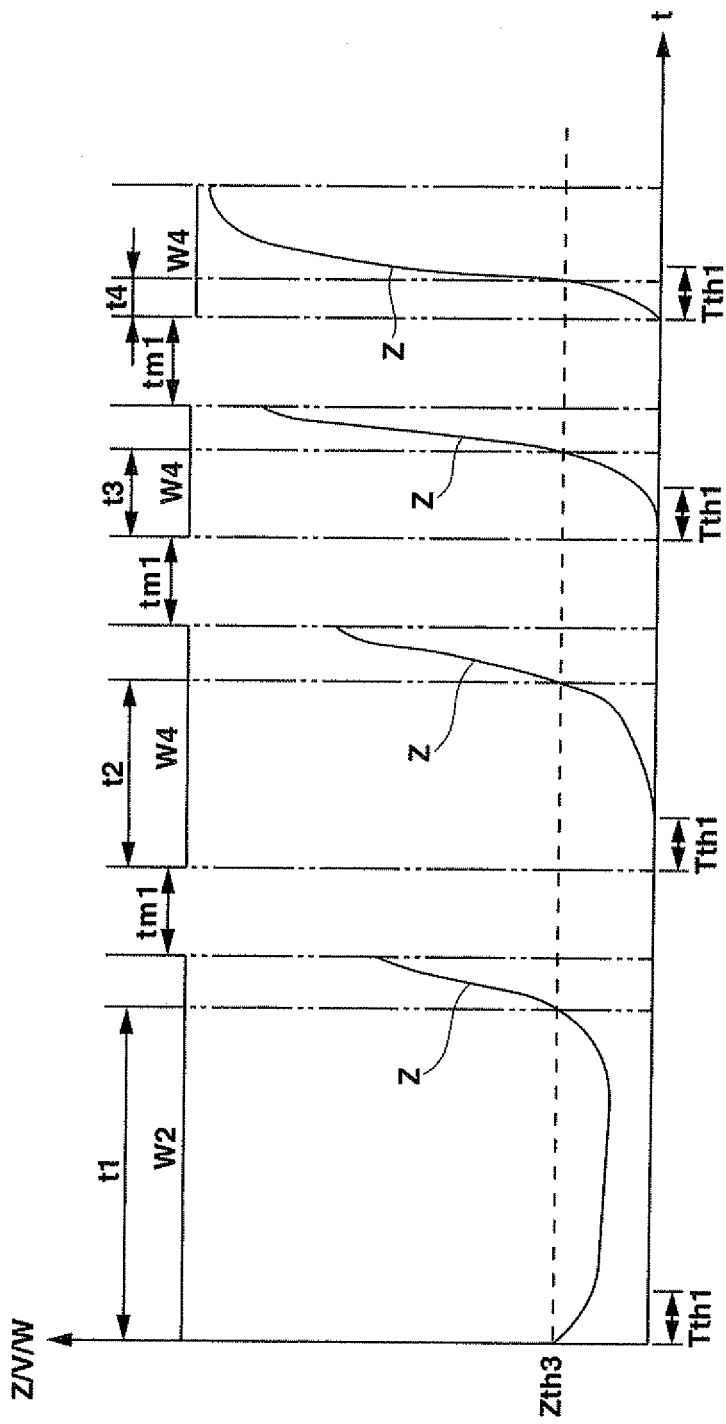
FIG. 9 is a graph that illustrates an example of changes accompanying the elapsed time in an impedance Z and an output power or a voltage according to the third embodiment of the present invention.

FIG. 8 is a flowchart that illustrates an example of a processing flow for determining a dehydration state of tissue according to the present embodiment. FIG. 9 is a graph that illustrates an example of changes accompanying the elapsed time in impedance Z and the output power or the voltage.

The processing of the flowchart shown in FIG. 8 starts when the foot switch 4 or the like is pressed.

First, the control portion 18 turns on the power supply circuit 11 to output a predetermined signal to the waveform shaping circuit 13, and thereby start output of high frequency power of a predetermined power value W2 from the output transformer 14 (step S31).

Further, the control portion 18 starts to measure a low impedance continuation time LZT that is a period in which the impedance Z is less than a predetermined threshold value Zth3 after starting the power supply (step S32).

Thereafter, the control portion 18 calculates and monitors the impedance Z of tissue based on electrical current value data and voltage value data input from the A/D converter 17.

In this connection, similarly to the first embodiment, the output control is performed so as to start from constant power control, and then switch to constant voltage control when the impedance Z reaches a predetermined value or more.

Next, the control portion 18 determines whether or not the calculated impedance Z is greater than or equal to the predetermined threshold value Zth3 (step S33). When the impedance Z is less than the predetermined threshold value Zth3, the result at step S33 is "NO", and the control portion 18 continues to monitor the impedance Z.

In this connection, a configuration may also be adopted in which, at step S33, the control portion 18 calculates the Z inclination as the rate of change in the impedance Z that is the calculated impedance value, and determines whether or not the Z inclination is greater than or equal to a predetermined threshold value to thereby determine the end of the low impedance continuation time LZT.

In FIG. 9, although the impedance Z temporarily drops immediately after the start of power output, thereafter the impedance Z rises accompanying evaporation of moisture in the tissue.

When the impedance Z becomes greater than or equal to the predetermined threshold value Zth3, the result at step S33 is "YES", and the control portion 18 ends measurement of the low impedance continuation time LZT (step S34). Hence, the time that is measured in this case is the time taken for the impedance Z to reach a value that is greater than or equal to the predetermined threshold value Zth3 during the high frequency power supply period in which a high frequency power is supplied.

In this connection, the threshold value Zth3 is set to a value that enables detection of a time of the first sharp rise in impedance shown in FIG. 3.

The control portion 18 calculates the Z inclination as the rate of change in the impedance Z that is the calculated impedance value, and determines whether or not the Z inclination is greater than or equal to the predetermined threshold value ZDth2 (step S35).

When the Z inclination is less than ZDth2, the result at step S35 is "NO" and no processing is performed.

When the Z inclination is greater than or equal to ZDth2, the result at step S35 is "YES", and next the control portion 18 determines whether or not the measurement value of the low impedance continuation time LZT that ended at step S34 is less than a predetermined value Tth1 (step S36).

When the low impedance continuation time LZT is not less than the predetermined value Tth1, the result at step S36 is "NO", and the control portion 18 stops output of the high frequency power for a predetermined time tm1 (step S37). After waiting for the lapse of the predetermined time tm1, the operation returns to step S31 and the control portion 18 performs processing to output a predetermined power W4.

In this connection, a configuration may also be adopted in which, at step S35, the control portion 18 determines whether or not the calculated impedance value is greater than or equal to a predetermined threshold value.

In the example shown in FIG. 9, after the first output period in which the Z inclination as the inclination in the impedance Z when the impedance Z rises becomes greater than or equal to the predetermined threshold value ZDth2, output of the high frequency power is stopped for the predetermined time tm1.

Further, after output of high frequency power in the second and third output periods, respectively, there is a stop period of predetermined time tm1, and thereafter output is started.

When the lapsed time is less than the predetermined value Tth1, the result at step S36 is "YES" and output of the high frequency power is terminated, i.e. stopped (step S38).

Since the fact that the lapsed time is less than the predetermined value Tth1 indicates that the tissue has entered a dehydrated state, it means that tissues are joined together with a strong joining force.

According to FIG. 9, in the fourth output period, since the low impedance continuation time LZT is less than the predetermined value Tth1, more specifically, this indicates the tissue is in a dry state, output of the high frequency power thereafter is stopped, i.e. output is terminated.

As described above, after there is an increase that is greater than or equal to a predetermined value in the calculated impedance Z, the control portion 18 performs control to intermittently supply a high frequency power, measures arrival times t1 to t4 until the impedance Z during a high frequency power supply period in which a high frequency power is supplied arrives at a value that is greater than or equal to predetermined threshold values Zth3, and when the measured arrival time is less than a predetermined time Tth1, the control portion 18 stops the supply of the high frequency power.

Accordingly, with the electrosurgical system 1 of the present embodiment also, since output of high frequency power is stopped by detecting a dry state of tissue, joining of tissue can be performed with a strong joining force.

Fourth Embodiment

Next, a fourth embodiment of the present invention is described.

According to the present embodiment, drying of tissue is determined by controlling to alternately supply and stop supply of a high frequency power, controlling a next high frequency power supply time based on a low impedance continuation time LZT, and detecting whether the low impedance continuation time LZT is shorter than a predetermined threshold value time.

The configuration of the apparatus of the present embodiment is the same as the configuration of the electrosurgical system 1 of the first embodiment as shown in FIG. 1. Hence, components that are the same as in the first embodiment are denoted by the same reference numerals and a description of those components is omitted.

Figure 10:
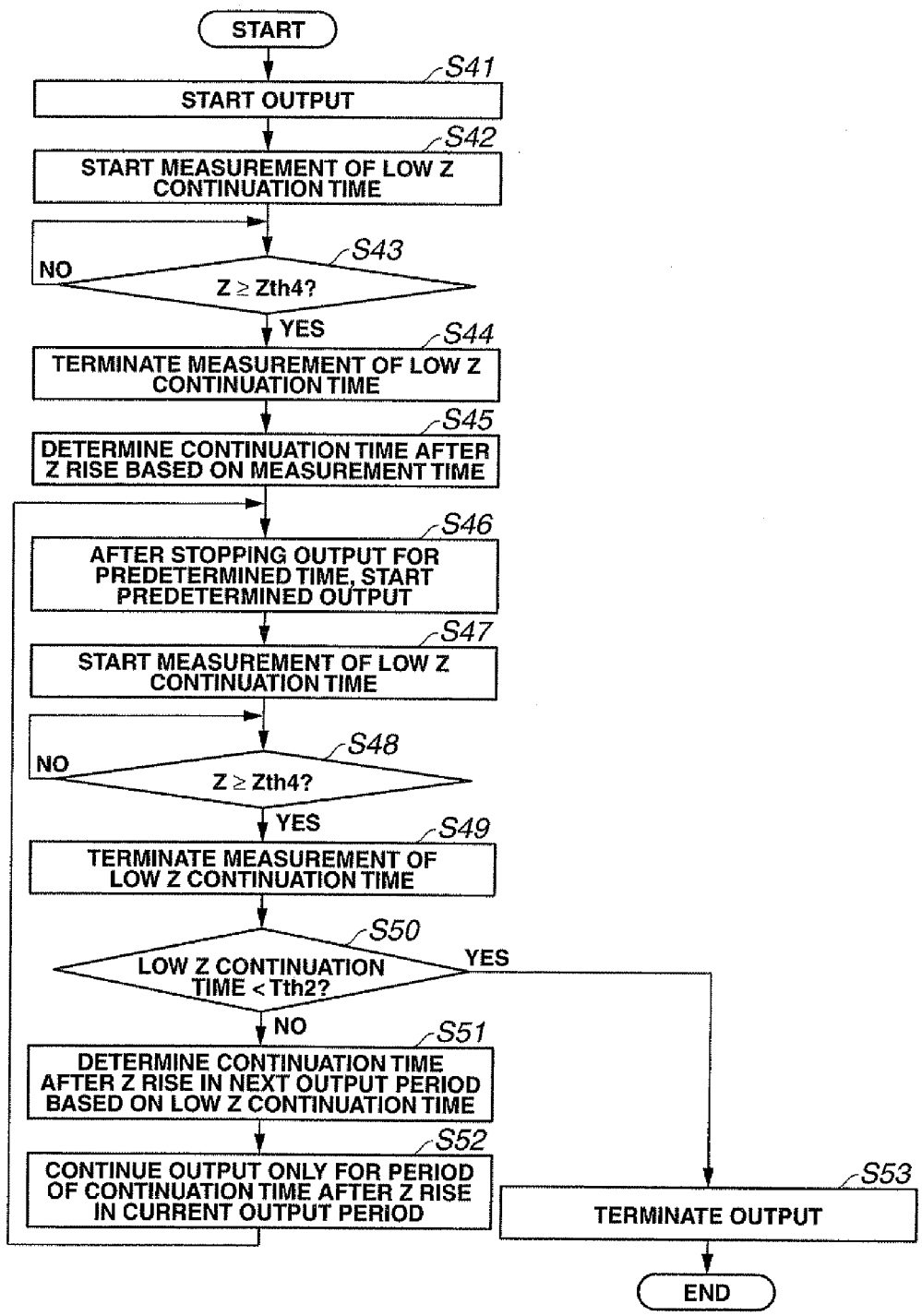
FIG. 10 is a flowchart that illustrates an example of a processing flow for determining a dehydration state of tissue according to a fourth embodiment of the present invention.
Figure 11:
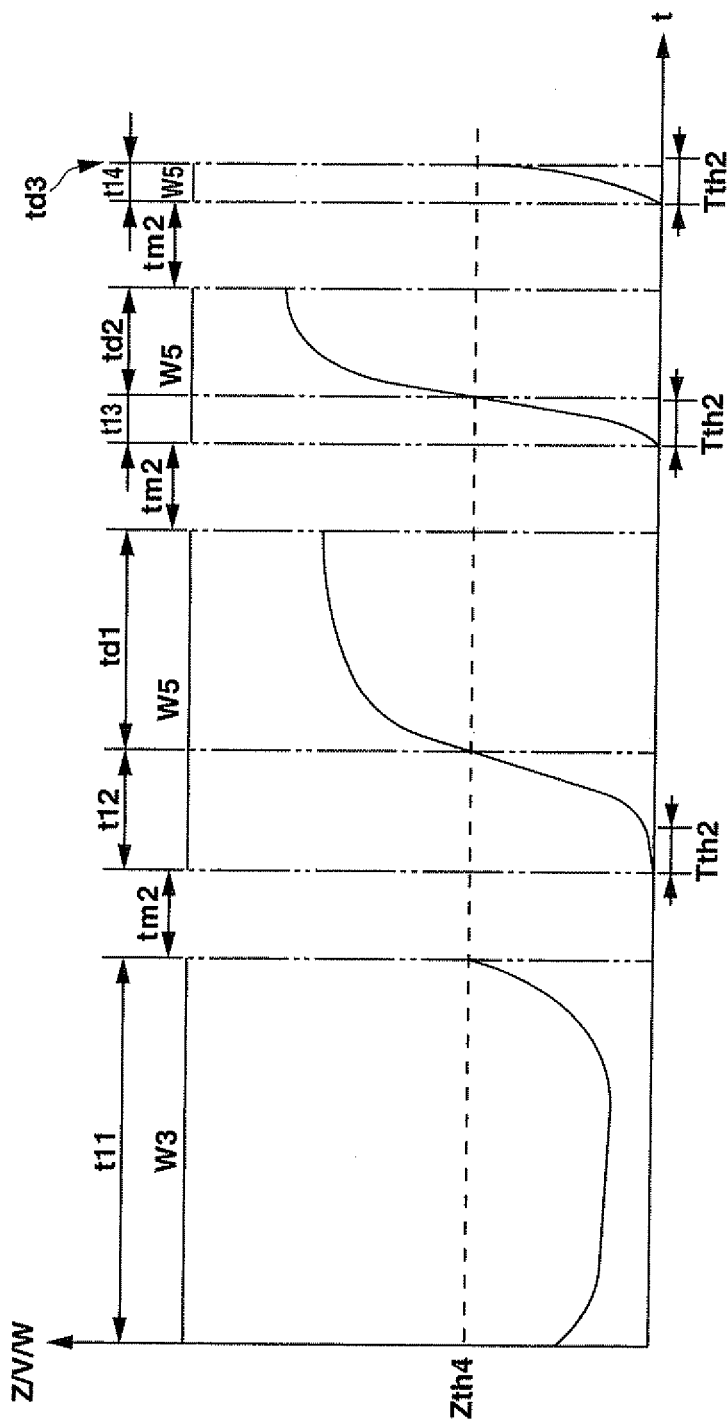
FIG. 11 is a graph that illustrates an example of changes accompanying the elapsed time in an impedance Z and an output power or a voltage according to the fourth embodiment of the present invention.
Figure 12:
FIG. 12 is a view that illustrates an example of table data for deciding a supply time of a high frequency power according to a fourth embodiment of the present invention.

FIG. 10 is a flowchart that illustrates an example of a processing flow for determining a dehydration state of tissue according to the present embodiment. FIG. 11 is a graph that illustrates an example of changes accompanying the elapsed time in impedance Z and the output power or the voltage. FIG. 12 is a view that illustrates an example of table data for determining the supply time of high frequency power.

The processing of the flowchart shown in FIG. 10 starts when the foot switch 4 or the like is pressed.

First, the control portion 18 turns on the power supply circuit 11 to output a predetermined signal to the waveform shaping circuit 13, to thereby start output of a high frequency power of a predetermined power value W3 from the output transformer 14 (step S41).

Thereafter, the control portion 18 calculates and monitors the impedance Z of tissue based on electrical current value data and voltage value data input from the A/D converter 17.

Further, the control portion 18 starts to measure a low impedance continuation time LZT from the time output of a predetermined power starts (step S42).

In this connection, similarly to the first embodiment, the output control is performed so as to start from constant power control, and then switch to constant voltage control when the impedance Z reaches a predetermined value or more.

Next, the control portion 18 determines whether or not the impedance Z as the calculated impedance value is greater than or equal to a predetermined threshold value Zth4 (step S43).

In this connection, a configuration may also be adopted in which, at step S43, the control portion 18 calculates the Z inclination as the rate of change in the impedance Z that is the calculated impedance value, and determines whether or not the Z inclination is greater than or equal to a predetermined threshold value to thereby determine the end of the low impedance continuation time LZT.

In FIG. 11, although the impedance Z temporarily drops immediately after the start of output of a high frequency power, thereafter the impedance Z rises sharply accompanying evaporation of moisture in the tissue.

When the impedance Z is less than ZDth4, the result at step S43 is "NO" and no processing is performed.

When the impedance Z becomes greater than or equal to Zth4, the result at step S43 is "YES" and the control portion 18 ends measurement of the low impedance continuation time LZT (step S44). Based on the measured time, the control portion 18 decides a continuation time td1 after a rise in the impedance Z with respect to the next high frequency power supply period (step S45). Hence, the time measured at step S44 (and step S49 described later) is an arrival time until the impedance Z in the high frequency power supply period in which a high frequency power is supplied arrives at the predetermined threshold value Zth4.

In this connection, the threshold value Zth4 is set to a value that enables detection of a time of the first sharp rise in impedance shown in FIG. 3.

This continuation time td after a sharp rise in the impedance Z is determined based on table data of an output continuation time determination table 21 shown in FIG. 12.

Data showing the correlation between the low impedance continuation time LZT and the output continuation time td after the low impedance continuation time in the next output is previously set and stored in an output continuation time determination table 21 shown in FIG. 12. More specifically, in the output continuation time determination table 21, output continuation times td that are previously set in accordance with the above described measured times, that is, arrival times (t11 to t14), are registered as additional times for a next high frequency power supply period.

FIG. 12 indicates that, when the low impedance continuation time LZT is less than a predetermined time Tth2, upon termination of the low impedance continuation time in the current output period, the output is terminated. Further, FIG. 12 indicates that, when the low impedance continuation time LZT is greater than or equal to the predetermined time Tth2 and less than a predetermined time Ta, the output continuation time td as an additional time after the low impedance continuation time in the next output period is "0" (zero). Furthermore, FIG. 12 indicates that, when the low impedance continuation time LIT is greater than or equal to the predetermined time Ta and less than a predetermined time Tb, the output continuation time td after the low impedance continuation time in the next output period is "5 seconds". Moreover, FIG. 12 indicates that, when the low impedance continuation time LZT is greater than or equal to the predetermined time Tb, the output continuation time td after the low impedance continuation time in the next output period is "10 seconds".

Subsequently, after stopping output of the high frequency power for a predetermined time tm2, the control portion 18 outputs a high frequency power of a predetermined power value W2 (step S46).

In the example shown in FIG. 11, after starting output of the high frequency power of a power value W3, the impedance Z reaches the threshold value Zth4, so that at step S45, the low impedance continuation time LZT is, for example, t11. Because t11 is greater than or equal to the predetermined time Tb, the control portion 18 determines that the output continuation time td1 after the low impedance continuation time in the next output period (second output period) is "10 seconds". Subsequently, at step S46, after the predetermined time tm2 elapses, output of a high frequency power for a second time is started.

The control portion 18 again starts measurement of the low impedance continuation time LZT from the time output of a predetermined voltage V5 starts (step S47).

The control portion 18 determines whether or not the measured impedance Z is greater than or equal to the predetermined threshold value Zth4 (step S48). When the impedance Z is less than the predetermined threshold value Zth4, the control portion 18 does not perform any processing and continues to supply the power.

When the impedance Z becomes greater than or equal to the predetermined threshold value Zth4, the control portion 18 terminates measurement of the low impedance continuation time LZT (step S49), and determines whether or not the low impedance continuation time LZT is less than the predetermined threshold value Tth2 (step S50).

When the low impedance continuation time LZT is greater than or equal to the predetermined threshold value Tth2, the result at step S50 is "NO", and the control portion 18 then determines a continuation time td after the impedance rise for the next output period based on the low impedance continuation time LZT (step S51).

The control portion 18 continues output for the amount of continuation time after the impedance rise in the current output period (step S52). Thereafter, the processing returns to step S46.

In the example shown in FIG. 11, since the low impedance continuation time LZT in the second output period is t12, and t12 is greater than or equal to the predetermined time Ta and less than the predetermined time Tb, an output continuation time td2 after the low impedance continuation time in the next output period (third output period) is determined as "5 seconds". Thus, output is continued for the continuation time td1 after the impedance rise in the current output period (second period), and after the continuation time td1 elapses the output is stopped.

In the third output period also, since the low impedance continuation time LZT is not greater than or equal to the threshold value Tth2, the continuation time td3 is determined as the continuation time after the impedance rise in the next output period. Further, since the low impedance continuation time LZT is t13 and the time t13 is greater than or equal to the predetermined time Tth2 and less than the predetermined time Ta, the output continuation time td after the low impedance continuation time for the next output period (fourth period) is set as "0" (zero).

At step S50, when the control portion 18 determines that the low impedance continuation time LZT is less than the predetermined threshold value Tth2, the control portion 18 terminates, i.e. stops, output (step S53).

In the case illustrated in FIG. 11, the control portion 18 determines in the fourth output period that the low impedance continuation time LZT is less than the predetermined threshold value Tth2 and stops output.

More specifically, since the fact that the low impedance continuation time LZT is less than the predetermined threshold value Tth2 indicates that the tissue is in a dry state, output of a high frequency power is stopped.

As described above, after there is an increase that is greater than or equal to the predetermined value Zth4 in the calculated impedance Z, the control portion 18 controls to intermittently supply a high frequency power and measures the arrival time until the impedance Z arrives at the predetermined threshold value Zth4 in the high frequency power supply period in which the high frequency power is supplied. Subsequently, in the next high frequency power supply period, the control portion 18 controls so as to supply a high frequency power during an additional time that is added to an arrival time as a set time that is previously set in accordance with measured arrival times t11 to t14, and when an arrival time is less than the predetermined time Tth2, the control portion 18 stops the supply of the high frequency power.

Accordingly, in the electrosurgical system 1 of the present embodiment, since the output of high frequency power is stopped by detecting a dry state of tissue, joining of tissues can be carried out with a strong joining force.

According to the electrosurgical apparatus of each of the above described embodiments, since output of high frequency power is stopped by detecting a dry state of tissue, joining of tissues can be carried out with a strong joining force.

The present invention is not limited to the above described embodiments, and various modifications and improvements can be made thereto without departing from the spirit and scope of the invention.

What is claimed is:

1. A method for controlling an electrosurgical apparatus for joining biological tissues, the method comprising:
a detection portion detecting a voltage and a current of a high frequency power that is output from a high frequency power supply portion for supplying the high frequency power to be applied to the biological tissues;
an impedance calculating portion calculating an impedance value between a pair of electrodes to which the high frequency power is applied and which grasps the biological tissues, based on respective values of the voltage and the current that are detected; and
a control portion controlling so as to stop supply of the high frequency power and output a predetermined voltage (Vd) for monitoring a state of the biological tissues for a predetermined time (tm) when there is an increase that is equal to or greater than a predetermined value in the impedance value calculated by the impedance calculating portion after starting supply of the high frequency power, and
if the impedance value calculated by the impedance calculating portion at an end of the predetermined time (tm) is equal to or greater than a first threshold value (Zth2) the control portion controlling so as to substantially stop supply of the high frequency power from the high frequency power supply portion, and
if the impedance value calculated by the impedance calculating portion at the end of the predetermined time (tm) is less than the first threshold value (Zth2) the control portion controlling so as to intermittently perform supply of the high frequency power and output of the predetermined voltage (Vd) and when the impedance value calculated by the impedance calculating portion at the end of the predetermined time period (tm) in which the predetermined voltage is output becomes equal to or greater than the first threshold value, substantially stop supply of the high frequency power from the high frequency power supply portion.

2. The method for controlling an electrosurgical apparatus according to claim 1, wherein, when the impedance value at the end of the predetermined time period, in which the predetermined voltage is output, is less than a second threshold value that is smaller than the first threshold value, a power value of the high frequency power to be supplied in a next high frequency power supply period is increased by a predetermined amount.

3. The method for controlling an electrosurgical apparatus according to claim 2, wherein, when the impedance value at the end of the predetermined time (tm) in which the predetermined voltage is output is less than the first threshold value and greater than or equal to the second threshold value, the control portion does not change a power value of the high frequency power to be supplied in a next high-frequency low power supply period.

4. A method for controlling an electrosurgical apparatus for joining biological tissues, the method comprising:
a detection portion detecting a voltage and a current of a high frequency power that is output from a high frequency power supply portion for supplying the high frequency power to be applied to the biological tissues;
an impedance calculating portion calculating an impedance value between a pair of electrodes to which the high frequency power is applied and which grasps the biological tissues, based on respective values of the voltage and the current that are detected;
a measuring portion measuring an arrival time until the impedance value calculated by the impedance calculating portion arrives at a value that is greater than or equal to a first threshold value after starting supply of the high frequency power; and a control portion controlling so as to stop supply of the high frequency power when there is an increase that is equal to or greater than a predetermined value (ZDth2) in the impedance value calculated by the impedance calculating portion, the control portion controlling so as to intermittently perform the supply of the high frequency power until there is an increase that is equal to or greater than the predetermined value (ZDth2) in the impedance value calculated by the impedance calculating portion and the stop of supply of the high frequency power for a first time period (tm1), when the arrival time measured by the measuring portion is equal to or greater than a predetermined time (Tth1), and the control portion controlling so as to substantially stop supply of the high frequency power from the high frequency power supply portion when the arrival time measured by the measuring portion becomes less than the predetermined time.

5. The method for controlling an electrosurgical apparatus according to claim 4, wherein the control portion determines whether or not there is an increase that is greater than or equal to the predetermined value in the impedance by comparing a rate of change per unit time in the impedance or an impedance value calculated by the impedance calculating portion with a predetermined threshold value.

\* \* \* \* \*